United States Patent [19]
Freitag et al.

[11] Patent Number: 5,223,436
[45] Date of Patent: Jun. 29, 1993

[54] TEST CARRIER FOR THE ANALYTICAL DETERMINATION OF A COMPONENT OF A LIQUID SAMPLE

[75] Inventors: Helmut Freitag, Indianapolis, Ind.; Anselm Rothe, Birkenau, Fed. Rep. of Germany; Klaus Pollmann, Indianapolis, Ind.

[73] Assignee: Boehringer Mannheim GmbH, Mannheim, Fed. Rep. of Germany

[21] Appl. No.: 244,852

[22] Filed: Sep. 14, 1988

[30] Foreign Application Priority Data

Sep. 30, 1987 [DE] Fed. Rep. of Germany ....... 3733084

[51] Int. Cl.[5] ............................................. G01N 33/49
[52] U.S. Cl. ...................................... 436/97; 422/56; 422/57; 422/58
[58] Field of Search ................ 422/56, 57, 58; 436/97

[56] References Cited

U.S. PATENT DOCUMENTS

| 4,477,575 | 10/1984 | Vogel et al. | 422/57 |
| 4,820,489 | 4/1989 | Rothe et al. | 422/58 |
| 4,861,712 | 8/1989 | Bartl et al. | 422/58 |
| 4,876,067 | 10/1989 | Deneke et al. | 422/58 |

FOREIGN PATENT DOCUMENTS

| 3130749 | 2/1983 | Fed. Rep. of Germany . |
| 3323973 | 1/1985 | Fed. Rep. of Germany . |

*Primary Examiner*—Robert J. Warden
*Assistant Examiner*—Timothy M. Mahon
*Attorney, Agent, or Firm*—Felfe & Lynch

[57] ABSTRACT

The present invention provides a test carrier for the analytical determination of a component of a liquid sample, especially of a body fluid, with a carrier layer, which is partly covered by a liquid-absorbing layer which contains a sample application zone and a transport zone, and a reagent layer which is in contact with the liquid-absorbing layer, wherein the reagent layer in contact with the liquid-absorbing layer is so arranged that it does not overlap with the sample application zone and is full-facedly in contact with the liquid-absorbing layer.

10 Claims, 1 Drawing Sheet

TEST CARRIER FOR THE ANALYTICAL DETERMINATION OF A COMPONENT OF A LIQUID SAMPLE

BACKGROUND OF THE INVENTION

The present invention is concerned with a test carrier for the analytical determination of a component of a liquid sample, especially of a body fluid, comprising a carrier layer, which is partly covered by a liquid-absorbing layer which contains a sample application zone and a transport zone, and a reagent layer which is in contact with the liquid-absorbing layer. The present invention is also concerned with the use of such a test carrier for the determination of a component of a liquid sample, especially of a body fluid.

Test carriers have achieved considerable importance in the analysis of liquids. In clinical chemistry, which involves the qualitative and quantitative analytical determination of components of body fluids, especially of blood and urine, the advantages thereof are especially appreciated. While the classical methods of working with liquid reagents require a plurality of handling steps, analytical determinations with the help of test carriers are characterized by extremely simple handling. In the analysis of urine, for example, test carriers are generally used in the form of test strips which are briefly dipped into the sample and thereafter evaluated either visually or with the use of appropriate apparatus. In the case of blood analysis, a drop of serum or, using especially advanced types of test carriers, a drop of blood is applied to a predetermined point of the test carrier.

The reaction of the sample liquid with the reagents present on the test carrier leads to a perceptible change of the test carrier and usually a change of color, brought about by the formation or liberation of a colored material. The reaction can also lead to the formation or change of a fluorescing substance or of a substance which can be perceived optically or in some other way. Test carriers for the determination of blood components are generally evaluated with the use of appropriate apparatus.

In the initial period of development of test carriers, these only possessed a single test layer upon which various reagents were combined in such a manner that even complicated reaction sequences were possible. However, single-layer test carriers do not permit chronologically defined courses of several reactions connected in sequence. This makes dependable quantitative determination of an analyte using kinetic measurements impossible. Furthermore, the stability of mixtures of different reagents is, in comparison with pure materials, often considerably reduced. This can also result in unreliable measurement values being obtained.

These considerations led to the development of test carriers in which reagents are present in different reagent layers and these can, furthermore, be arranged on a test layer in such a manner that a chronologically defined course of successively connected reactions is possible.

Federal Republic of Germany Patent Specification No. 31 30 749 describes test carriers for the determination of various parameters in serum, plasma or whole blood in which the carrier layer is formed by a longitudinal base film, upon which a liquid-absorbing layer is arranged. A rectangular covering film is fixed with one edge to the base film, which is just as wide as the base film but considerably shorter. The fixing point is in the region of the end of the liquid-absorbing layer. On the one side of the covering film facing the base foil a reagent layer, such as a reagent film is presented. The covering film with the reagent film forms a flap, the fixing thereof on to the base film thereby being such that the flap, in the resting state, does not touch the liquid-absorbing layer but can be brought into contact therewith by external manipulation. It is possible, using such a device to divide up the chronological course of a determination reaction into steps. For this purpose, the sample is first applied to a sample application zone on the liquid-absorbing layer which, when whole blood is used as sample, must be such that the erythrocytes are separated off and held back, and the erythrocyte free sample is sucked into the subsequent transport zone of the liquid-absorbing layer. The sample can then, if this is necessary, be tempered within the liquid-absorbing layer. Such is necessary, e.g., in enzymatic determinations. At a definite point of time, the covering film with its reagent layer is pressed down on to the base film and thus brought into contact with the liquid-absorbing layer. By means of this full-faced contact, the sample contained in the liquid-absorbing layer passes into the reagent layer of the flap and there, at a definite point of time, initiates a reaction which results in a detectable signal, such as a color change.

It is an important disadvantage of such test carriers that chronologically decoupled reactions in the sense of chemical, enzymatic or immunological reaction steps of a total reaction sequence necessary for the detection of a component material of a body fluid cannot be carried out. This is because as soon as the reagent layer arranged on the flap contacts the liquid absorbing layer, all of the reagents react with all of the sample components, rendering it impossible to carry out a chronological series of reactions. Further, treatment of the sample so as to condition it chemically, enzymatically or immunologically prior to the actual reaction to be measured, is not possible.

Admittedly, the reagents required for the total reaction sequence or for the conditioning can, depending upon the corresponding partial reactions, be divided into several reagent layers which, independently of one another, can be successively pressed on to the base film. Carrying out these steps to determine an analyte in a body fluid using an apparatus is extremely laborious and expensive. Furthermore, each reagent layer requires a definite volume of liquid for wetting. The more reagent layers used, the more sample volume necessary for wetting all of the layers. This is a considerable disadvantage since it is desired that only the smallest possible amounts of body fluids, for example blood, be used for the investigations.

Chronologically decoupled reactions are, in the case of the test carriers described in Federal Republic of Germany Patent Specification No. 31 30 749, in principle also possible by impregnating the liquid-absorbing layer with appropriate soluble reagents. However, this possibility suffers from the deficiency that, because of the liquid transport within the liquid-absorbing layer, impregnated reagents become enriched in the liquid front and chromatographic effects can appear which result in the formation of spatial concentration gradients and, in the end, in non-reproducible and falsified measurement results. In addition, not every material useful in a liquid absorption layer is suitable for impregnation with reagents.

Furthermore, since the liquid-absorbing layer contacts erythrocytes when the sample is whole blood, those reagents which undergo exchange reactions with erythrocytes and which disturb the detection reaction, cannot be used for the impregnation of this layer. Thus, for example, the use of materials for the impregnation of the liquid-absorbing layer which act hemolytically result in lysing of the red blood corpuscles and release of their components which can considerably disturb the test, for example due to their inherent color or due to their chemical, enzymatic or immunological reactivity. Under certain circumstances, for example in the case of the determination of bilirubin in whole blood, because of the liberation of hemoglobin from the erythrocytes, completely false measurement values are obtained.

Similar test carriers are also known which contain layers impregnated with reagents in the sample application zone, over the liquid-absorbing layer but in absorbent contact with this and possibly under an erythrocyte-separating layer, as shown in FIG. 3. Such a device is described in U.S. Pat. No. 4,477,575 and DE OS 33 23 973 (U.S. Ser. No. 77,003). In the case of the application of the sample, the materials impregnated in the reagent layer also come into contact with erythrocytes and products which result from this exchange action can pass into the transport zone of the liquid-absorbing layer where, as already stated, they can then disturb the desired reaction considerably. Therefore, the same limitations described supra apply here as well.

The last-described test carriers also possess a disadvantage in that, depending upon the nature and manner in which the sample is applied to the sample application zone, the reagent layers can be wetted by the sample to differing extents. Thus, for example, in the case of a given size of the sample application zone, the same sample volumes can be applied so that only a small surface of these reagent layers come into contact with the sample. It is also possible, however, to carry out the sample application so that the reagent layers are completely wetted by the sample. The extent of the wetting depends, therefore, upon the dexterity of the person applying the sample. The concentration of the reagent which dissolves in the sample during the wetting of the reagent layer present in the sample application zone is thus also dependent upon this parameter. As a result, although the control of reagent in the sample are supposed to be exactly adjusted, in fact inexact, greatly scattered measurements and completely false results occur.

These problems indicate, therefore, that there is a need for test carriers which only require a small amount of sample, which permit the analysis of blood without the danger of exchange actions with erythrocytes, such as hemolysis, in which the concentration of reagents in the sample are controlled and exactly adjusted and with which reactions can be chronologically decoupled.

SUMMARY OF THE INVENTION

Thus, according to the present invention, there is provided a test carrier for the analytical determination of a component of a liquid sample, especially of a body fluid, with a carrier layer, which is partly covered by a liquid-absorbing layer which contains a sample application zone and a transport zone, the absorbing layer having an exposed surface opposite said carrier in said liquid transport zone, and a reagent layer which is in contact with the liquid-absorbing layer. The reagent layer in contact with the liquid-absorbing layer is so arranged that it does not overlap with the sample application zone and is full-facedly in contact with the liquid-absorbing layer.

In the case in which reactions are to be chronologically decoupled in a definite manner, the test carrier according to the present invention has at least one reagent layer which, by external manipulation, can be brought into direct contact with the exposed surface liquid-absorbing layer and which can cover the reagent layer in permanent contact with the liquid-absorbing layer.

In this connection, as sample application zone there is to be understood the total region of a test carrier and not only the application layer where the sample is applied. Especially when the sample is whole blood, there is hereunder to be understood the whole region which contains erythrocytes after the application of the sample.

The transport zone is to be understood to be the whole part of the liquid-absorbing layer which is not a part of the sample application zone.

Overlapping of the sample application zone and the reagent layer in contact with the liquid-absorbing layer is always present when parts of the layer project into the zone and thus planar contact takes place. However, when used herein "overlapping" also refers to the situation where the sample application zone and the reagent layer abut one another and only touch with their outer limits or edges. According to the present invention, the sample application zone and the reagent layer in contact with the liquid-absorbing layer are arranged spatially separated.

In the scope of the present invention, the liquid-absorbing layer and the reagent layer present in the transport zone of the test carrier are in contact with one another. However, this does not mean that they must be in direct immediate contact with one another. Indirect contact, for example by one or more layers which permits a liquid exchange, is not to be excluded, however direct contact of the liquid-absorbing layer and the reagent layer in contact is preferred.

These considerations also apply for a reagent layer of the test carrier which, by external manipulation, can be brought into contact with the liquid-absorbing layer. There, too, after the production of the contact between the reagent layer and the liquid-absorbing layer, direct, immediate contact is produced. However, it is also possible that both layers are in contact with one another via one or more other layers which permit a liquid exchange.

In any case, in the test carrier according to the present invention, the reagent layer in contact with the liquid-absorbing layer must be so arranged that both lay over one another in such a manner that, by a liquid exchange which is vertical with regard to the liquid-absorbing layer, they are in contact with one another.

The same applies to a test carrier with which chronologically decoupled reactions are to be carried out. In this case, the reagent layer in contact with the liquid-absorbing layer and the reagent layer to be brought into contact by external manipulation with the liquid-absorbing layer must be so arranged that both of them, after external manipulation, come to lie over one another in such a manner that they are in contact with one another and permit liquid exchange which is vertical with regard to the liquid-absorbing layer. As a rule, this is achieved by pressing on of the layer to be brought into contact with the liquid-absorbing layer in the direction of the carrier layer.

The test carrier according to the present invention differs in its construction from known test carriers in that a reagent layer in contact with the liquid-absorbing layer is so arranged that it is no longer in direct, immediate contact with the sample application zone. However, liquid exchange is naturally possible. Thus, sample component held back in the sample application zone do not come into contact with the reagent layer.

In a preferred test carrier according to the present invention, a reagent layer in contact with the liquid-absorbing layer is inserted in the end of the transport zone remote from the sample application zone in such a manner that, within the transport zone, there is produced a change of direction of the liquid flow produced after sample application through the liquid-absorbing layer. A change of the liquid flow in the direction vertical to the liquid-absorbing layer is especially preferred. According to the present invention, such a change of the liquid flow is produced because the reagent layer in contact with the liquid-absorbing layer consists of absorbent material and can exchange liquid with the liquid-absorbing layer within the transport zone full-facedly but not over the edges.

The reagent layer can be embedded in the liquid-absorbing layer in such a manner that the reagent layer lies in the interior of this layer so that a liquid-absorbing layer lies not only above but also below the reagent layer, i.e., the liquid absorbing layer surrounds the reagent layer. The reagent layer can also be arranged over the liquid-absorbing layer so that it is in direct contact with another reagent layer which, by external manipulation, for example by pressing, is brought into contact with the liquid-absorbing layer.

Especially preferred is an embodiment of the test carrier according to the present invention in which a reagent layer is arranged so that it is outside of the sample application zone between the carrier layer and the liquid-absorbing layer. Advantageously, it is fixed on to the carrier layer, preferably with a melt adhesive strip, so that it is held in position and cannot slip.

The liquid-absorbing layer can consist of a variety of materials. Especially preferred are papers, fleece and those film layers which, because of an open structure having numerous capillary slots, have a considerable take-up ability for liquids. This take-up ability for liquids must be so great that the amount of liquid absorbed therein suffices to wet all the reagent layers necessary for the detection reaction completely.

The reagent layer used in the test carriers according to the present invention are materials which are impregnated with reagents, such as fabrics, which have absorbent properties. By arranging the reagent layer in contact with the liquid-absorbing layer on the end of the transport zone and remote from the sample application zone, it is possible to obtain a good and uniform liquid exchange with the liquid-absorbing layer so that, within a relatively short time, a homogeneous solution results within this zone of the test carrier. There can also be used water-soluble films which contain the necessary reagents and which, upon contact with the sample are dissolved. Such films can consist of a high molecular weight, polymeric, water-soluble material. Especially preferred as film formers are those materials which are also used as binding or swelling agents or as thickeners, for example xanthan gum.

Because of its special arrangement, the test carrier according to the present invention displays surprising advantages in comparison with the test carriers known from the prior art. Thus, the concentration of the reagent dissolved from the reagent layer in contact with the liquid-absorbing layer in the sample is independent of the nature of the type or mode of sample application to the sample application zone and thus can be adjusted exactly and in a controlled manner. This is especially important for those tests in which it is of decisive importance to have exact control of the reagent used, for example, chronologically decoupled reactions.

Surprisingly, using the test carrier of the present invention, a homogeneous solution is obtained within the transport zone within a very short time. Because of the complete and uniform wetting of the reagent layer in contact with the liquid-absorbing layer with sample liquid, chromatographic effects do not occur.

Since reagents in the reagent layer of the described test carrier do not come into contact with erythrocytes when whole blood is analyzed, materials which could enter into an exchange reaction with erythrocytes and disturb the test and thus could not be used in prior art devices can now be used. For example, using the test carrier according to the present invention, it is possible to use hemolytically acting materials, for example dyphylline, in the reagent layer in contact with the liquid-absorbing layer. This is especially important for tests for bilirubin in whole blood since in such tests hemolysis, and thus the efflux of component materials of red blood corpuscles lead to completely falsified results. Such tests are especially sensitive towards hemolysis but can, nevertheless, be carried out with the test carrier according to the present invention with an excellent and reproducible exactitude not before seen in the prior art.

While it was known from the prior art that each additional layer in a test carrier required more sample volume, this does not apply to the test carrier according to the present invention. On the contrary, the reagent layer in contact with the liquid-absorbing layer contributes, because of its absorbent properties, to the withdrawal of the liquid more from the sample application zone and to the collection on the other end of the liquid-absorbing layer. As a result, sufficient liquid is available for wetting the reagent layer to be brought into contact therewith by external manipulation.

DETAILED DESCRIPTION OF PREFERRED EMBODIMENTS

Figure 1:
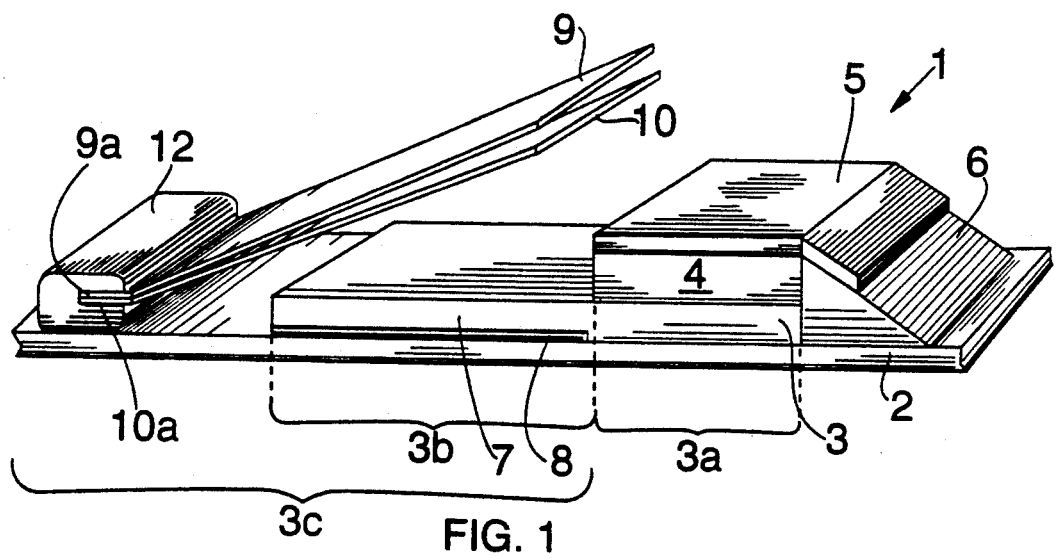
FIG. 1 shows a preferred embodiment of the test carrier described herein.

The test carrier 1 illustrated in FIG. 1 has a base film 2 which serves as a carrier layer for a liquid-absorbing layer 3 lying full-facedly thereon. The base film 2 is narrow and extends longitudinally. The layers arranged thereon have the same breadth as the base film 2 but extend only over a part of its length.

The total test region of the test carrier 1 can be subdivided into a sample application zone 3a and into an evaluation region 3c. Within the evaluation region 3c there is also present a transport zone 3b of the liquid-absorbing layer 3. The transport zone 3b includes the region of the liquid-absorbing layer 3 which does not belong to the sample application zone 3a.

In the sample application zone 3a is provided, above the liquid-absorbing layer 3, a plasma separation layer 4 which, for protection against damage, is covered with a covering mesh 5. The plasma separation layer 4 and the covering mesh 5 only cover a part of the liquid-absorbing layer. Not only the liquid-absorbing layer 3 but also the plasma separation layer 4 and the covering mesh 5 are fixed at one end by a melt adhesive strip 6 to the base film 2.

In the transport zone 3b, below the liquid-absorbing layer 3, a reagent layer 7 is fixed with a melt adhesive strip 8 to the base film 2.

In the evaluation region, the test carrier has a flap indicated in its entirety by 9 and a reagent carrier 10. The flap 9 and the reagent carrier 10 are each rectangular and have the same breadth as the base film 2. With one of their short edges 9a and 10a, respectively, they are fixed on to the base film 2 in such a manner that, prior to use they are not in contact with the liquid-absorbing layer 3 but, by external manipulation, for example by pressing, they can be brought into contact with this.

The flap 9 consists of a covering film which is preferably made of a synthetic polymer which is permeable to visible light. A material which is especially preferred for this purpose is, for example, polycarbonate film.

For carrying out an analysis, an amount, for example 30 ul of blood, are applied to the covering mesh 5 and the plasma separation layer 4. The sample trickles through the synthetic resin mesh and the plasma separation layer 4 into the liquid-absorbing layer 3, the erythrocytes in the blood thereby being separated off (further details can be obtained from U.S. Pat. No. 4,477,575). In the liquid-absorbing layer 3, the plasma so formed is transported in the longitudinal direction of the test carrier into the evaluation region 3c. For this purpose, the liquid-absorbing layer 3 has capillary transport properties in this direction, i.e. in the direction of its planar extension.

The liquid-absorbing layer 3 and the plasma separating layer 4 are preferably made from glass fibres (cf. U.S. Pat. No. 4,477,575). However, they can also be made from some other material which fulfills the abovementioned conditions.

After the liquid-absorbing layer 3 has been rapidly filled with plasma, the sample passes, with change of the previous liquid transport direction, by diffusion, into the reagent layer 7 where reaction of the sample with the reagents impregnated on the layer takes place. Because of the short diffusion paths, a homogeneous solution is formed within a short period of time of the order of magnitude of within one minute.

The reagent layer 7 preferably has an open composite structure for the liquids and can be made of the most varied materials, for example synthetic or natural polymers. Of the possible synthetic materials, polyamide and especially polyester fabrics are preferred. Of the natural materials, paper is especially preferred. A quite especially preferred material for the reagent layer 7 is tea bag paper, for example one with a weight per unit surface area of about 10 to 15 g/cm$^3$ and preferably of 12 g/m$^3$ made of manila long-fibre hemp.

After the expiry of a predetermined period of time after the application of the sample, at a precisely determined point of time, a further reaction is initiated by pressing down the flap 9 on to the liquid-absorbing layer 3. Because of the pressing down of the flap 9, the reagent carrier 10 is brought into contact with the plasma reacted with the reagent impregnated in the reagent layer 7, whereby, with a renewed change of the liquid transport direction, this is sucked into the carrier and there brought into a further reaction which finally leads to a detectable signal, for example to a color change.

The reagent carrier 10 and the reagent layer 7 can consist of the same or different carrier material. However, in principle, the material of the reagent carrier 10 is selected from the same choice of materials as are suitable for the reagent layer 7.

Surprisingly, in the pressed-together state of the test carrier 1, when layers 7, 3 and 10 form a medium whose thickness corresponds to all layers between flap 9 and base film 2, a homogeneous solution forms very quickly. Thus the detectable signal in the solution can be determined here. This determination preferably takes place with the use of apparatus and, on the basis of the relative great layer thickness, is very precise. Surprisingly, it has been shown that, due to the fact that the liquid-absorbing layer is comparatively thick and is preferably made of a fibrous material, the quality of optical measurement is not impaired. Especially good measurement precision is even obtained when the liquid-absorbing layer 3 is produced from a material with a comparatively small optical absorption ability so that it is penetrated by the measurement light of an appropriate remission photometer. When the material of the layer 7 and of the carrier 10 also display such optical properties, then either the flap 9 of the base film 2 but preferably the base film 2, must be diffusely reflective. The measurement light is thereby reflected back through the layers and detected by the measurement receiver of a reflection photometer. Since the measurement light penetrates twice through the full layer thickness of the layers 3, 7 and 10, the optical layer thickness forming the basis of the measurement is comparatively great, which results in excellent sensitivity of the measurement.

While the embodiment shown in FIG. 1 has only one reagent layer 7 in the transport zone 3b and only one reagent carrier 10 under the flap 9, it is to be pointed out that, under certain circumstances, it can, of course, also be advantageous to arrange several reagent layers 7 over or next to one another between the carrier layer and the liquid-absorbing layer or to arrange one or more layers above and one or more layers below the liquid-absorbing layer. It is also possible to provide reagent layers not only in the sample application zone but also in the transport zone. Thus, for example, it is conceivable, in order to simplify erythrocyte separation, to arrange above the plasma separation layer 4 and below the covering mesh 5 a reagent layer impregnated with an erythrocyte separating substrate such as those described in DE OS 33 23 973 which corresponds to U.S. Ser. No. 077,003 and, at the same time, to place reagents in the reagent layer 7 between the carrier layer and the liquid-absorbing layer. In such a construction the plasma separation layer may be made, e.g., of a glass fiber fleece.

It can also be advantageous to place several reagent carriers 10 under the flap 9 or between the reagent carrier 10 and the flap 9, to introduce a reagent layer on the flap 9, for example in the form of a film.

When a chronologically defined decoupling of the steps necessary for the determination reaction is not required, flap 9 can be omitted as can be reagent layers present thereon which first, by external manipulations, are, at a given point of time, brought into contact with the liquid-absorbing layer. All the reagents necessary for the test can then, as described hereinbefore, be so arranged that they are in permanent contact with the liquid-absorbing layer.

With this choice of possibilities, it is to be pointed out that depending upon the test to be carried out, reasons can be given to vary the described basic principle of the test carrier according to the present invention without its advantageous actions thereby being decisively changed.

The following Examples are given for the purpose of illustrating the present invention:

EXAMPLE 1

Figure 2:
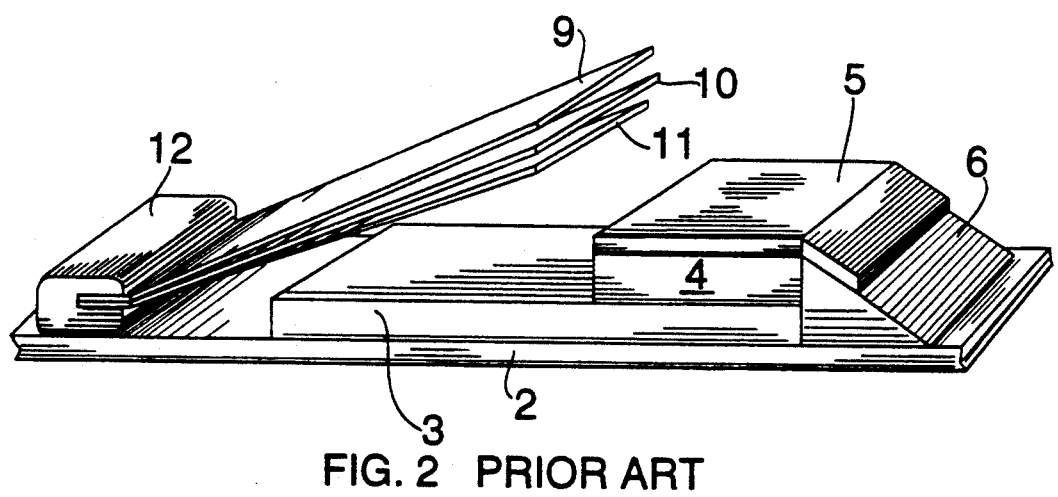
FIGS. 2 and 3 show prior art devices.

TEst carrier for the determination of bilirubin in blood according to FIG. 2 (Prior art)

a) Production of reagent carrier 11

260 g/liter dyphylline in water are impregnated on to tea bag paper 212 (Schoeller & Hoesch, Gernsbach, Federal Republic of Germany) and dried for 10 minutes at 50° C.

b) Production of reagent carrier 10

9 g/liter 2-methoxy-4-nitrophenyldiazonium tetrafluoroborate in water are impregnated on to tea bag paper 212 and dried for 10 minutes at 50° C.

Test strips according to FIG. 2 are produced with the reagent carriers 10 and 11. Reagent carriers 10 and 11, together with 0.2 mm thick covering film of polycarbonate ("Pokalon", Lonza, Weil, Federal Republic of Germany), are fixed via an adhesive point 12 on to a base film 2 upon which has already been applied a 15 mm wide glass fiber fleece 3 (thickness 0.25 mm, weight per unit surface area about 25 g/m$^2$) so that the free end of the carrier 10 and 11, as well as the flap 9, still extends 6 mm over the fleece. On the glass fiber fleece 3 is applied a plasma separation layer 4, also of glass fiber fleece, both of which are connected with the base film 2 by a nylon protective mesh by means of a melt adhesive strip 6.

The strips are used to measure bilirubin in samples using a "Reflotron" apparatus (Boehringer Mannheim GmbH, Mannheim, Federal Republic of Germany). The evaluation takes place via empirically determined function curves.

Measurement results

I. Unsatisfactory dyphylline action since no true chronologically decoupled pre-reaction and incomplete liberation of the bound bilirubin takes place in the sample.

For reference purposes, native sera are measured. The Reflotron measurements are carried out with whole blood. The results obtained are given in the following Table:

| actual wet refernce method value in mg./dl. | Reflotron measurement, mg./dl | difference from actual value % |
| --- | --- | --- |
| 0.8 | 0.6 | 25 |
| 1.2 | 0.9 | 25 |
| 1.4 | 0.7 | 50 |
| 1.8 | 1.3 | 28 |
| 2.5 | 1.4 | 44 |

II. Dependency of the measurement values on the dosing volume.

A supplemented control sample with free bilirubin has an actual value of 5.2 mg/dl. Ten measurement values are determined:

| dosing volume (ul.) | 26 | 28 | 30 | 32 | 34 |
| --- | --- | --- | --- | --- | --- |
| measuring value (mg./dl.) | 2.5 | 4.1 | 5.2 | 5.2 | 5.4 |
| vK (%) | 20.7 | 8.3 | 3.5 | 3.8 | 4.2 | vK means variation coefficient.

EXAMPLE 2

Figure 3:
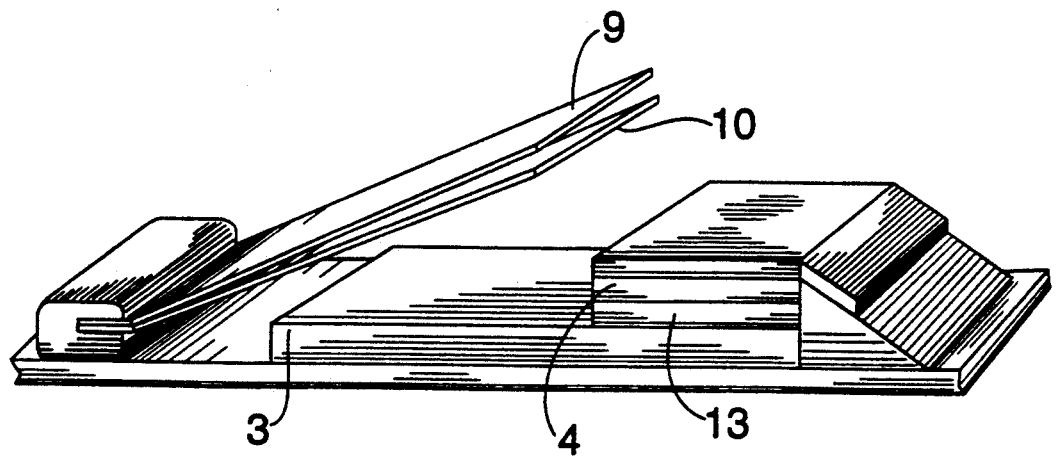

Test carrier for the determination of bilirubin in blood according to FIG. 3 (Prior art)

Test strips according to FIG. 3 are produced with the use of the reagent carriers from Example 1a) and 1b).

The diazonium paper 10 is placed under the flap 9 and the dyphylline paper 13 (which corresponds to the carrier 11 produced in Example 1) is placed between the two glass fiber fleece 3 and 4. The test carrier in FIG. 3 is produced in a manner analogous to that described in Example 1.

The measurement results with serum and plasma are satisfactory.

When the analysis is carried out with blood, depending upon the sample, varying strong hemolysis takes place. Hemoglobin gets under the measurement eye, is measured by the apparatus and simulates bilirubin values which are too high. In the case of a typical blood sample, the following values are measured:

| plasma | 3.2 mg/dl |
| --- | --- |
| blood | 8.5 mg/dl. |

EXAMPLE 3

Test carrier according to the present invention for the determination of bilirubin in blood according to FIG. 1

Test strips according to FIG. 1 are produced with the use of test carriers from Example 1a) and 1b).

The diazonium paper 10 is present under the flap 9 and the dyphylline paper 7 is placed under the glass fiber fleece 3. The production of the test carrier in FIG. 1 takes place analogously to the description given in Example 1.

Measurement results

I. Sufficient dyphylline action

Clinical tests give an excellent agreement between the wet reference method DPD in native serum (Boehringer Mannheim GmbH) and the bilirubin from whole blood with a test carrier according to FIG. 1.
28 sera
x = DPD value
r = correlation coefficient
y = bilirubin value with a test carrier according to the present invention
y = 0.046 + 1.01x; r = 0.999

II. No hemolysis

Blood and plasma separated therefrom are measured with a Reflotron $^R$ apparatus (Boehringer Mannheim GmbH, Mannheim, Federal Republic of Germany).

|  | sample 1 | sample 2 | sample 3 |
| --- | --- | --- | --- |
| blood | 0.72 | 1.30 | 4.53 |
| plasma | 0.70 | 1.28 | 4.59 mg./dl. |

III. No volume problems within the usual dosing limits of 28 to 32 ul

Measurement with the control sample from Example 1 (actual value 5.2 mg bilirubin/dl).

| dosing volume (ul.) | 26 | 28 | 30 | 32 | 34 |
| --- | --- | --- | --- | --- | --- |
| measurment value (mg./dl.) | 3.8 | 4.9 | 5.2 | 5.1 | 5.3 |
| vK (%) | 8.6 | 4.5 | 3.2 | 2.9 | 3.5 |

It will be understood that the specification and examples are illustrative but not limitative of the present invention and that other embodiments within the spirit and scope of the invention will suggest themselves to those skilled in the art.

We claim:

1. Test carrier useful in determining a component of a liquid sample, comprising:
   (a) a carrier layer;
   (b) a liquid absorbing layer which is positioned on said carrier layer and which contains a sample application zone and a liquid transport zone, said liquid absorbing layer having an exposed surface opposite said carrier layer in said liquid transport zone,
   (c) a first reagent layer which is in contact with said liquid absorbing layer in full faced array in said transport zone, but does not contact said sample application zone and
   (d) at least one additional reagent layer, said additional reagent layer positioned in said test carrier to permit direct contact between said additional reagent layer and said exposed surface of said liquid absorbing layer.

2. Test carrier of claim 1, wherein said first reagent layer is positioned between said carrier layer and said liquid absorbing layer.

3. Test carrier of claim 2, wherein said first reagent layer is fixed to said carrier layer via a melt adhesive.

4. Test carrier of claim 1, wherein said first reagent layer is hemolytic.

5. Test carrier of claim 1, wherein said liquid absorbing layer comprises paper, fleece, or a film.

6. Test carrier of claim 1, wherein said reagent layer comprises reagent impregnated absorbent fibers or a reagent impregnated film soluble in a sample liquid.

7. Test carrier of claim 1, wherein said additional reagent layer comprises a reagent impregnated absorbent fibers or a reagent impregnated film soluble in a sample liquid.

8. Test carrier of claim 1, wherein said reagent layer is positioned in said test carrier fixed onto said carrier layer and away from said sample application zone.

9. Method for determining a component of a liquid sample comprising contacting a liquid sample with a device of claim 1 and determining a reaction therein indicating presence or amount of said component.

10. Method of claim 9 for determining bilirubin in blood or in samples derived from blood.

* * * * *